United States Patent [19]
Goymann et al.

[11] Patent Number: 5,702,484
[45] Date of Patent: Dec. 30, 1997

[54] ENDOPROSTHESIS

[75] Inventors: Volkmar Goymann, Essen; Emmanuel Anapliotis; Juergen Darga, both of Berlin, all of Germany

[73] Assignee: BIOMET Deutschland GmbH, Berlin, Germany

[21] Appl. No.: 585,388

[22] Filed: Jan. 11, 1996

[30] Foreign Application Priority Data

Jan. 11, 1995 [DE] Germany ............... 195 01 995.4

[51] Int. Cl.$^6$ ........................................ A61F 2/36
[52] U.S. Cl. ........................... 623/23; 623/1
[58] Field of Search ...................... 623/16, 18, 19, 623/20, 22, 23

[56] References Cited

U.S. PATENT DOCUMENTS

| | | |
|---|---|---|
| 4,978,357 | 12/1990 | Goymann et al. . |
| 5,061,286 | 10/1991 | Lyle ............... 623/23 |
| 5,152,795 | 10/1992 | Sioshansi et al. ............... 623/23 |

FOREIGN PATENT DOCUMENTS

| | | | |
|---|---|---|---|
| 0243585 | 11/1987 | European Pat. Off. ............... 623/23 |
| 0295200 | 12/1988 | European Pat. Off. . | |
| 3913874 | 5/1990 | Germany ............... 623/23 |
| 4028038 | 3/1992 | Germany ............... 623/23 |
| 8801492 | 3/1988 | WIPO ............... 623/23 |

*Primary Examiner*—Debra S. Brittingham
*Attorney, Agent, or Firm*—Spencer & Frank

[57] ABSTRACT

An endoprosthesis for a cement free anchorage in a bone having a longitudinal direction comprises a prosthetic shank to be secured in the bone in the longitudinal direction of the bone. The prosthetic shank has a proximal end and a distal end and includes three plate-like blades arranged in parallel and presenting a cross-sectional profile that has an open configuration. A first one of the blades constitutes a central web and a second and third ones of the blades constitute side walls which enclose, at least partially, the central web and extend, at least partially, in parallel, in a direction of the central web. The prosthetic shank further includes bridges connecting the side walls with the central web. A region adjacent the distal end of the prosthetic shank is in the shape of a scoop and the blades are joined at least at the distal end to form a common cutting edge. A collar including a pin for receiving a ball joint is attached to the proximal end of the prosthetic shank.

22 Claims, 4 Drawing Sheets

ENDOPROSTHESIS

BACKGROUND OF THE INVENTION

The invention relates to an endoprosthesis for a cement free anchorage, comprising a prosthetic shank to be secured in a bone in the longitudinal direction thereof, where the shank carries at the proximal end a collar with a pin for receiving a ball joint, and the prosthetic shank comprises several plate-like blades which are arranged interconnected in parallel and its cross-sectional profile has an open configuration.

Hip endoprostheses are known which comprise a prosthetic head, a prosthetic collar and a prosthetic shank anchored in the medullary space of the femur of a patient without using cement, after the medullary space has been correspondingly prepared by partially removing the spongiosa.

When the prosthesis shank is secured in the medullary space of the femur without using cement, a shank structure is used which has a preferably porous surface so that the anchorage of the shank in the medullary space, which must be as firm as possible, is supported by spongiosa material growing into it.

The removal of the spongiosa, however, must be regarded as a non-physiological local disturbance resulting in damage. When such damage occurs, the stress resistance of an implanted endoprosthesis and especially the age-related adaptability thereof are impaired.

European Patent EU-B1 0 295 200 discloses an endoprosthesis which allows an anchorage of the prosthetic shank in the medullary space of the femur, without the spongiosa of the intertrochanteric region having to be removed.

The known endoprosthesis is intended for an anchorage without using cement. It has a prosthetic shank, to be secured in a femur bone in the longitudinal direction, said prosthetic shank carrying, at its proximal end, a collar with a pin to receive a ball joint. The prosthetic shank is made of a plurality of parallel, interconnected, plate-like blades so that its cross-section has an open configuration. The blades have cutting edges along the periphery.

The main disadvantage of the above endoprosthesis, however, is that the distal cutting edges are substantially perpendicular relative to the driving-in direction of the prosthesis, so that the insertion requires considerable force. The relatively long distal cutting edges have the further disadvantage that, in the main, the prosthesis can only be positioned in the intertrochanteric spongiosa region, otherwise an undesirable medial or lateral pressure force in the bone interior is produced.

This is a further disadvantage of the known endoprosthesis resulting in a non-uniform force distribution because of the forces being introduced primarily into the femoral part substantially proximally, the distal bone part thereby not being functionally stressed. This leads to an atrophy and does not stimulate the bone functionally, as required, for it to grow firmly to the endoprosthesis.

This leads to a premature loosening of the endoprosthesis and makes a further operation necessary. Such an operation, however, is always of disadvantage to the patient, since the endoprosthesis can only be removed by destroying a considerable part of the bone material which basically makes growing-in of a new endoprosthesis more difficult and to some extent impossible.

A further disadvantage of the known endoprosthesis is the fact that, although standard models are available for different femur sizes, they are not adapted to the individual shape of the proximal femur of a patient so that the disadvantageous initiation of force into many endoprostheses is further increased and the available bone substance is not used optimally.

SUMMARY OF THE INVENTION

The invention has the object of providing an endoprosthesis of the above kind which ensures that the physiology of the medullary space including the intertrochanteric and subtrochanteric spongiosa is maintained and the operational technique simplified without a pre-chiselling or pre-drilling being necessary and which enables an optimal physiological force initiation and provides, at the same time, a larger contact surface for the adherence of the bone material.

The above and other objects are accomplished according to the invention by the provision of an endoprosthesis for a cement free anchorage in a bone having a longitudinal direction, comprising: a prosthetic shank to be secured in the bone in the longitudinal direction of the bone and having a proximal end and a distal end, the prosthetic shank comprising three plate-like blades arranged in parallel and presenting a cross-sectional profile that has an open configuration, a first one of the blades constituting a central web and a second and third ones of the blades constituting side walls which enclose, at least partially, the central web and extend, at least partially, in parallel, in a direction of the central web, the prosthetic shank further including bridges connecting the side walls with the central web, wherein a region adjacent the distal end of the prosthetic shank is in the shape of a scoop and the blades are joined at least at the distal end to form a common cutting edge; and a collar including a pin for receiving a ball joint attached to the proximal end of the prosthetic shank.

The invention is based on the finding that when an endoprosthesis is fitted whilst maintaining the spongiosa structures, the biological metabolism is significantly neither disturbed nor are the conditions for the supply of blood basically affected. When the physiology of the medullary space and of the intertrochanteric and subtrochanteric spongiosa is maintained, suitable anatomical conditions are provided for re-operations and an optimal adaptability to age-related bone changes is ensured.

According to the invention, the endoprosthesis enables a reliable securement of the blades without the spongiosa structure having to be further prepared, for example, by pre-cutting or rasping in order to be able to drive the blades of the endoprosthesis into the spongiosa. The shaping of the blades is such that the force necessary for the driving-in of the prosthesis is suitably decreased. One significant requirement for the driving-in of the shank is that all surfaces of the part of the endoprosthesis complex which are to be driven in are arranged parallel to one another and parallel relative to the femur axis, i.e. at right angles to the cross-section.

This approach offers significant advantages with respect to the operating technique since no rasping or pre-drilling is necessary, thus resulting in a considerable saving in time and a reduced risk of infection as well as preventing a via falsa.

Since, when the prosthetic shank is knocked in, the blades, which are constructed as plate-like surfaces, extend into the subtrochanteric spongiosa region, it is possible, on the one hand, to increase the contact surface for the growth of the bone material and to enable, on the other hand, an advantageous force initiation into the femur bone while the implanted prosthesis is subjected to stress.

According to the preferred embodiments of the invention, the prosthetic shank has three blades which are constructed as a centre web and two side walls which embrace, at least partially, the centre web. The centre web is mainly responsible for the force initiation from the pin, which carries the ball joint, into the prosthetic shank. In order to reduce the pressure load on the spongiosa to a minimum when driving the prosthetic shank into the bone, the blades at the distal end of the shank are combined in the form of a scoop, while forming a common cutting edge. In this way, the substantially uniform blades all taper distally in a streamlined shape.

In order to provide suitable conditions for the driving-in of the shank, the medial boundary edges of the blades forming the shank are substantially S-shaped, as illustrated in a further embodiment of the invention.

The prosthetic shank has an m-cross-sectional profile, the central arm of the profile projecting medially beyond the outer arms thereof. As the cutting edge is positioned at the distal end of the shank and the blades are guided in parallel, the spongiosa portions may move within the free space delimited by the blades, without the spongiosa structure being significantly destroyed. Here, the spongiosa is only cut open once during the insertion process so that the largest part of the cut surface may then readapt correctly.

Since the shape of the endoprosthesis, according to the invention, enables it to be attached to the femur of the patient, with utmost care given to the spongiosa, a safe physiological i.e. proximal force initiation is produced, whereby the spongiosa structures provide extremely reliable support and allow the transfer of considerable pressure forces.

In order to ensure the stability of the prosthetic shank, the arms of the shank section are interconnected by means of narrow crosspieces. Here, it is especially advantageous if, in each case, two of the crosspieces, which are distributed over the entire shank length at substantially the same spacing and which connect one or the shank side walls with the central blade, are positioned at the same height and are provided with a distally oriented cutting edge. These narrow connecting crosspieces not only stabilise the prosthetic shank but, at the same time, provide further possibilities of securement for the spongy structures in the intertrochanteric and sub-trochanteric region of the bone and only increase the resistance slightly when the prosthetic shank is driven in. The scoop-like construction of the end which is driven in first ensures a precise guidance which means that the driving-in can be carried out with little force. This is especially due to the face that the blades of the transverse reinforcements connecting the structure are also provided with cutting edges in the driving direction.

By providing the blade-shaped construction with transverse reinforcements, the cross-section of the walls provides the only resistance to the driving-in operation. The body tissue which positions itself in between the blades during the driving-in operation forms, together with the prosthetic material, a sandwich structure which has a high stability with respect to loads placed upon it. As the back is of a compact, round construction, a closed contact surface is formed for the initiation of force into the surrounding bone structure in the region subjected to the main load. Apertures within the side walls reduce its weight and enable the adherence or attachment of additional elements for asymmetrical adjustment when used in the left or right half of the body.

According to another advantageous embodiment of the invention, openings are provided at the proximal end of the prosthetic shank. These openings extend distally, in parallel relative to one another and to the shank axis. The distal end of the openings comes to rest in the space between the blades of the shank, which is defined by the m-shaped cross-section. These openings make it possible to equalise the pressure in a simple manner during the driving-in of the prosthetic shank into the femur and also allow the passage of any existing body fluid.

A further advantageous embodiment of the with the invention is characterised by the provision of recesses and/or openings in the proximal end of the blades forming the side walls of the shank. In this way, additional cavities are created into which the spongiosa material may grow so that the complex indented spongiosa structure is utilised for the transfer of the occurring forces, on the one hand, and an optimal connection of the endoprosthesis with the bone is ensured, on the other hand, with only a limited or no risk of a loosening. A circular construction of the openings may, for example, be suitable in order to be able to mount cylindrical support members, which may, preferably, be endogenic, spongiosa material or a bioporous foreign material and which extend at right angles to the axis of the prosthetic shank and further stabilise the implant by giving support on the inner bone wall. The recesses in the side walls are preferably in the form of a circular segment and extend to the lateral side of the shank, so that the cross-section of the shank may only be m-shaped for half the length of shank.

A further development of the prosthesis has advantageously a shank whose lateral wall has several slots, the individual slots which extend parallel to the shank axis being formed by a proximal and a distal connection, as well as a connection of the blades with the crosspiece in the centre of the shank. Such a shank construction further improves the possibilities of the growing-in of the implant.

The endoprosthesis according to the invention is preferably made of titanium. It is preferably manufactured by means of vacuum casting.

In order to improve the growing-in of spongiosa material further, it is advantageous if the inner wall regions of the an open modular constructed prosthetic shank are coated. It is especially suitable if an artificial spongiosa in the form of a bioporous material, for example hydroxyapatite ceramic material or a plasma spray having a layer thickness of 50 to 100 µm, is applied.

BRIEF DESCRIPTION OF THE DRAWINGS

Advantageous further developments of the invention are characterised or described in more detail below with reference to the drawings, illustrating the preferred embodiment of the invention. Shown are.

DETAILED DESCRIPTION OF THE INVENTION

Figures 1, 1A:
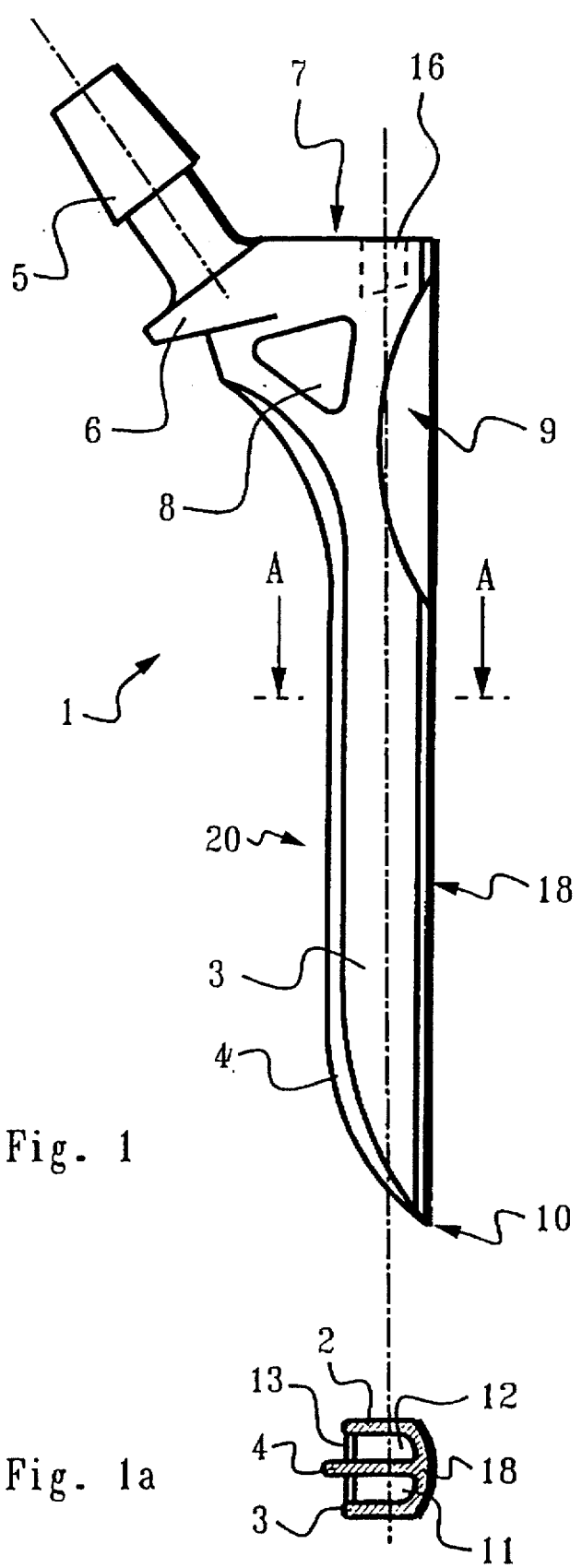
FIG. 1 a side view of the preferred embodiment of the invention.
FIG. 1a a view of a section along the line A . . . A as shown in FIG. 1.

The endoprosthesis 1 shown in FIGS. 1 and 1a has a shank 20 comprising three blades 2, 3, 4 which are arranged in parallel and extend from the proximal to the distal end. At the proximal end the blades 2, 3, 4 end in a prosthetic collar 6 which has a pin 5 to receive a ball joint (not shown).

The cross-section profile of the prosthetic shank 20 has an open configuration in the form of an M, the blades being in the form of a central web 4 and two side walls 2, 3 which enclose, at least partially, the central web 4. The lateral boundary edges of the blades 2, 3, 4 end in the lateral shank wall 18 which extends substantially rectilinearly from the proximal to the distal end. The shank 20 opens out in a streamlined fashion at the proximal end and tapers in a streamlined fashion at the distal end, the medial boundary edges of the blades being substantially S-shaped. In order to drive the shank prosthesis 1 easily into the bone without preparing the medullar space by drilling or rasping, the medial boundary edges of the blades 2, 3, 4 at the distal end of the prosthetic shank 20 are combined like a scoop while forming a joint cutting edge 10. In so doing, the spongiosa is cuttingly divided in the longitudinal direction and fills the free spaces 12, 13 within the cross section of the shank.

The relatively thin walls of the blades and the resilience of the spongiosa ensure a good contact between the prosthetic shank 2 and the bone material. This makes a safe growing-in of the prosthesis possible which is necessary when subjected to stress.

The openings or recess 8, 9 in the side walls 2, 3 within the proximal shank region of the prosthesis 1, as well as the crosspieces 13 distributed over the shank length provide further possibilities to secure the spongiosa. The openings 8 are in the form of triangles with rounded-off edges. The recesses 9, which are in the form of circular segments, extend from the lateral end of the shank to the centre and provide a cross-sectional profile of the proximal portion of the shank 20, which is open on either side.

The prosthetic collar 6 at the proximal end 7 of the shank 20 has two openings 16 which are arranged in parallel to one another, and extend from the proximal to the distal end in the direction of the shank axis. The distal end of the openings 16 opens out into the spaces 11 and 12 formed between the blades 2, 3, 4 of the shank 20 because of the m-shaped cross-sectional profile. The openings 16 enable an easy equalisation of pressure during the driving-in of the prosthetic shank 20 into the femur bone and also allow the passage of any body fluid.

Figures 2, 2A:
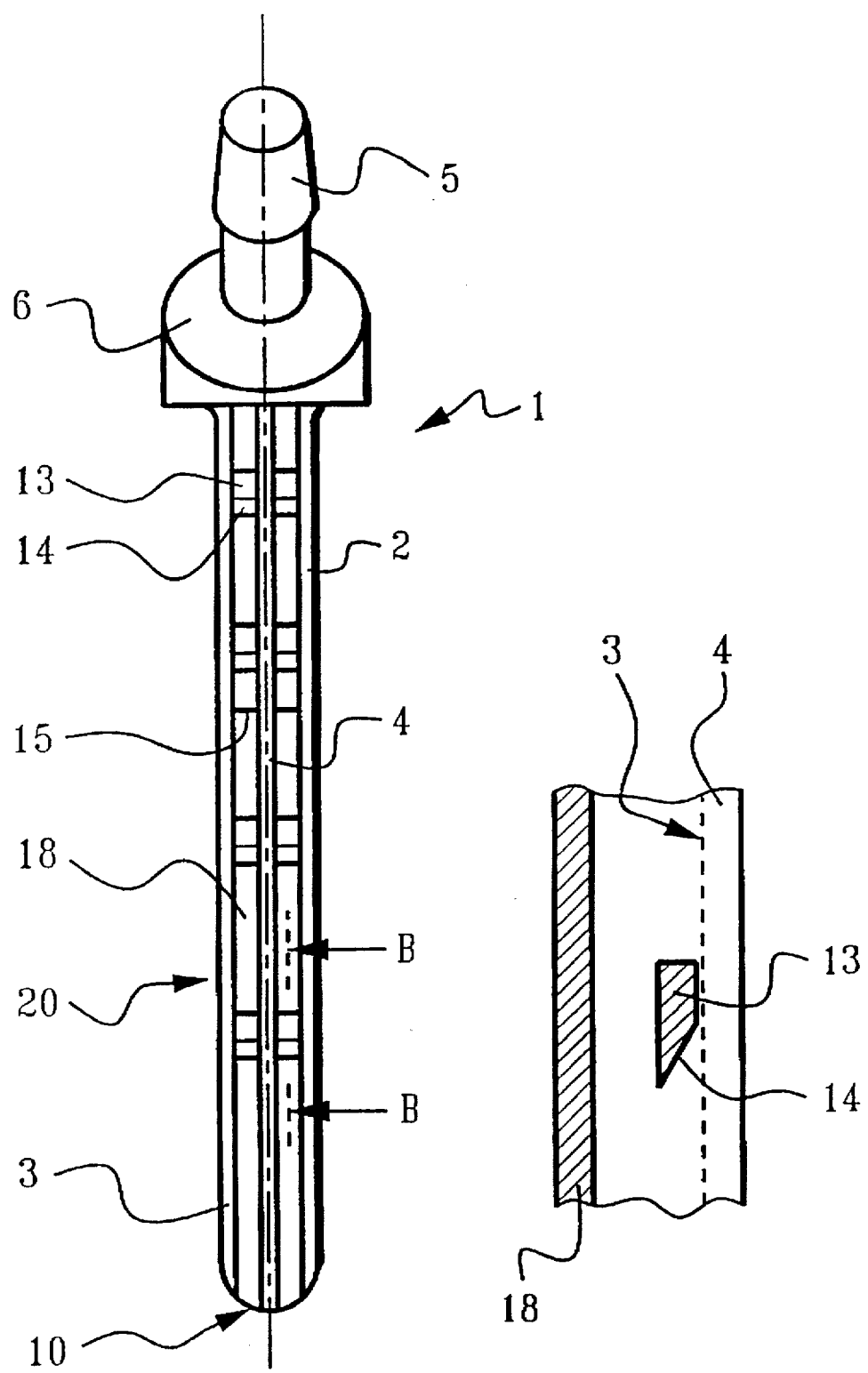
FIG. 2 the illustration of the prosthesis shown in FIG. 1 viewed from the left.
FIG. 2a the view of a section along the line B . . . B as shown in FIG. 2.

A medial view of the endoprosthesis 1, according to the invention, is shown in FIG. 2. The crosspieces 13 connecting the blades 2, 3, 4 are uniformly distributed over the length of shank 20. They extend at right angles to the shank axis and, as shown in FIG. 1a, they connect the free ends of the side walls 2, 3 of shank 20 forming the m-shaped section, with the central web 4 thereby increasing the stability of the shank and providing additional possibilities for anchoring to the spongiosa structures in the intertrochanteric and subtrocanteric region of the bone. Here, it is of special advantage if, in each case, two of the crosspieces 13, which are arranged along the entire length of the shank at substantially the same spacing and which each connect one of the side walls 2, 3 of the shank with the central blade 4, are positioned at the same height. The crosspieces 13 are provided with a distally oriented cutting edge 14 so that there is only a negligible increase in resistance when the prosthetic shank 20 is driven into the bone. This construction of the crosspieces and the scoop-like cutting edge 10 of the distal end of the shank makes it possible to suitably reduce the stress on the femur when the prosthetic shank is driven into the spongiosa structure of the bone. The shape of the cutting edge 14 is shown in FIG. 2a illustrating a sectional view along line B . . . B as shown in FIG. 2.

As the prosthetic shank 20 has recesses in the proximal region (cf. position 9 as shown in FIG. 1), it has no closed lateral wall 18. The corresponding wall edge 15 is positioned above the shank centre. Therefore, the spongiosa structures of the bone are able to fully embrace the side walls formed by the blades 2, 3 and the central web of shank 20, within the proximal portions thereof so that the stability of the implant in the bone is increased further.

The central web 4 of shank 20 is connected, via prosthetic collar 6, with the pin 5 which receives a ball joint, thereby providing suitable conditions for the force to be initiated centrally when the prosthesis is subjected to stress.

Figure 3:
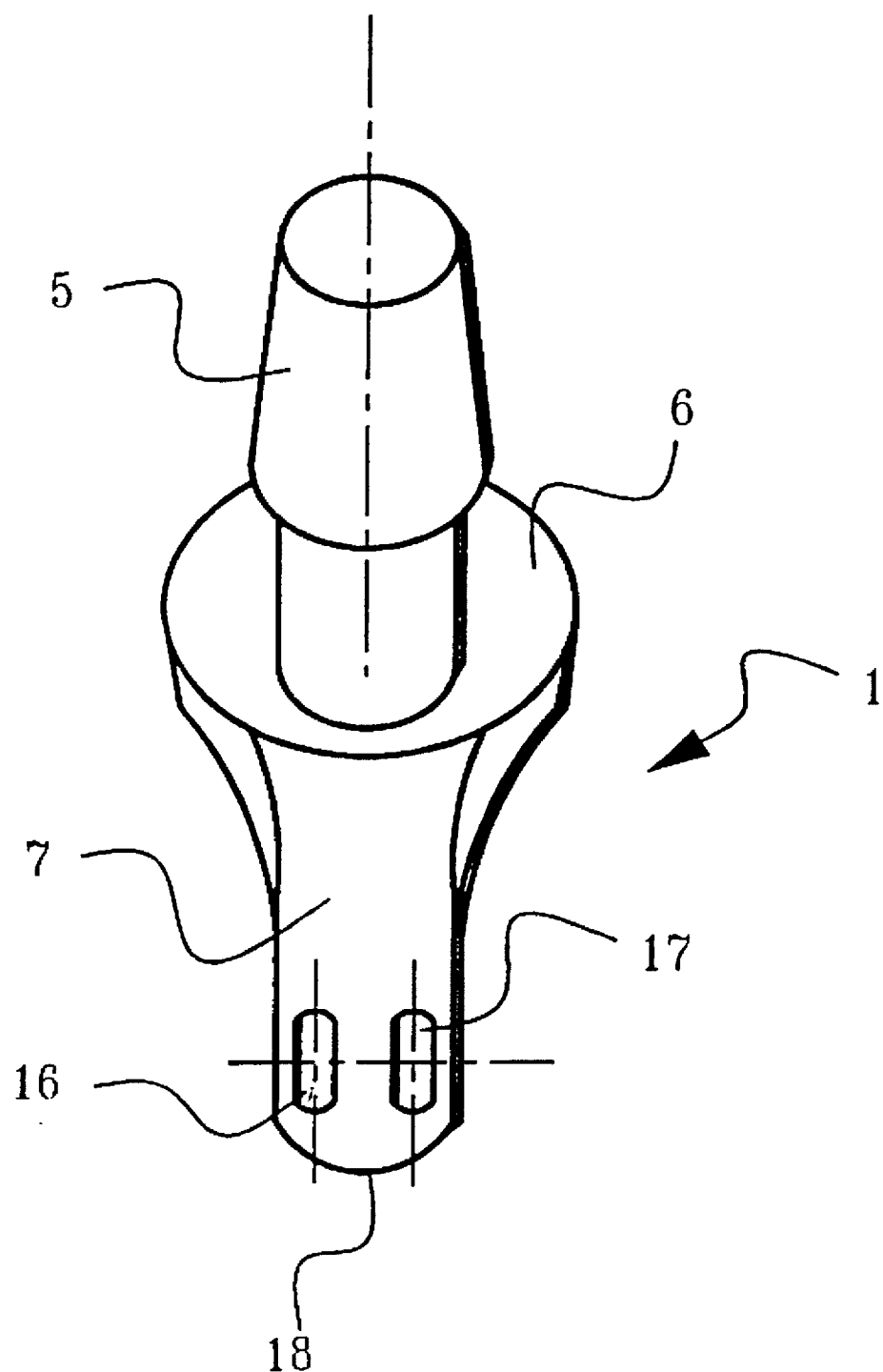
FIG. 3 the illustration of the prosthesis shown in FIG. 1, viewed from above.

A top-plan view of the endoprosthesis 1 illustrated in FIGS. 1 and 2 is shown in FIG. 3. At the proximal end 7 of the prosthetic shank there are two openings 16, 17 on the side remote from the prosthetic collar 6, carrying the pin 5, said openings being connected to the spaces between the shank blades (cf. positions 11, 12 and 2, 3, 4 as shown in FIGS. 1 and 1a). The lateral wall of the prosthetic shank is denoted by 18. The opening 16, 17, extend in parallel to one another and to the shank axis, in the distal direction. The openings 16, 17 allow for the pressure to be equalised in suitable manner during the driving-in of the prosthetic shank into the femur bone and also permit the passage of any body fluid present.

Figures 4, 4A:
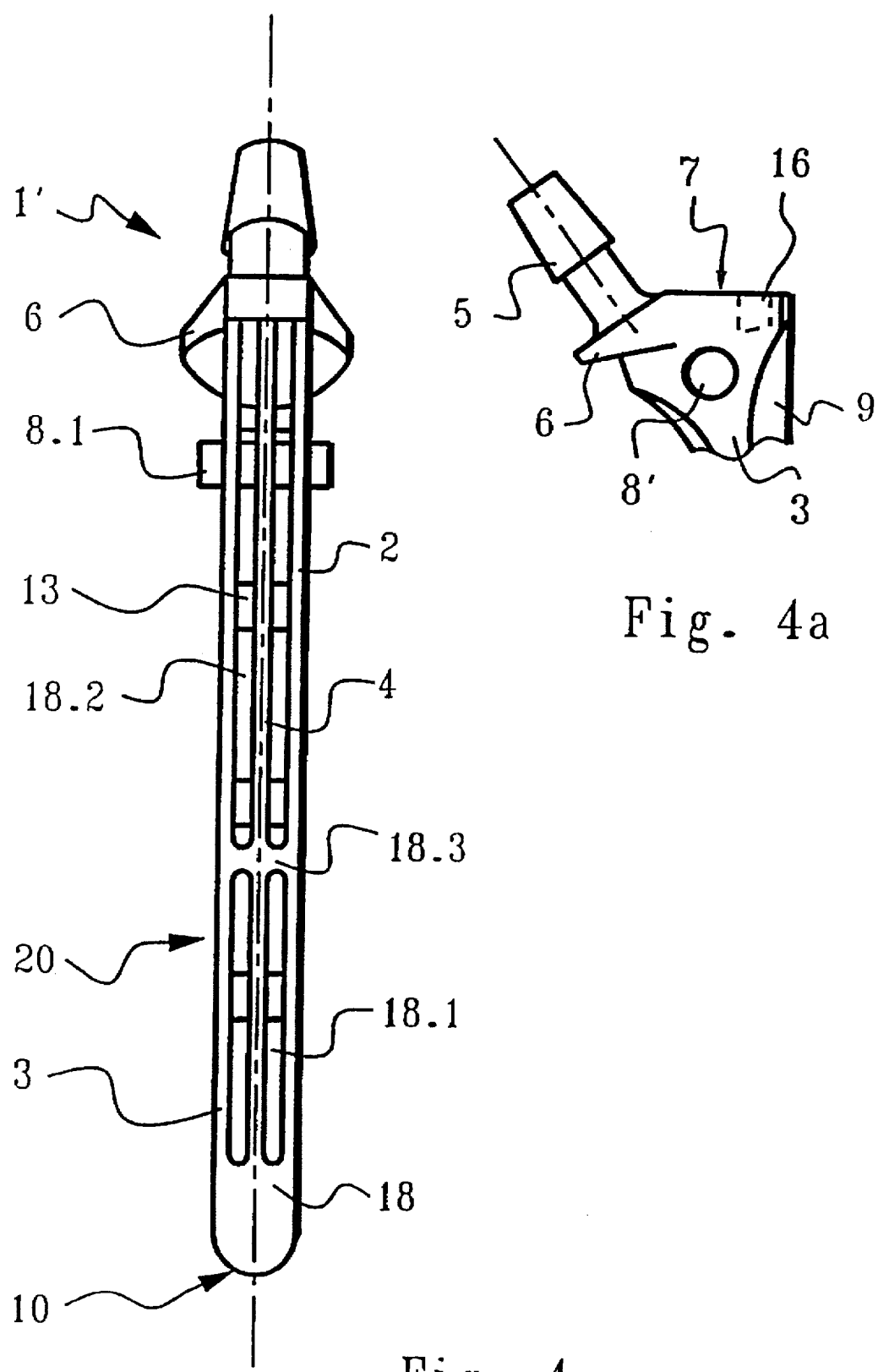
FIG. 4 an advantageous further development of the invention, viewed from the side.
FIG. 4a a side view of the proximal region of the prosthesis shown in FIG. 4.

The shank 20 of the prosthesis 1' shown in a lateral view in FIG. 4, has slots 18.1 and 18.2 in its lateral wall 18, which extend from the proximal to the distal end. These slots are formed by the blades 2, 3, 4 only being interconnected at their distal end thus forming a scoop-like cutting edge 10, as well as being interconnected in the shank centre by a narrow crosspiece 18.3 and at the proximal end by the prosthetic collar. In combination with the crosspieces 13 on the medial side of the shank 20, on which the cutting edges are formed (cf. position 14 as shown in FIG. 2a), the crosspiece 18.3 ensures a sufficient stability of the prosthetic shank. The slotted shank wall 18 further improves the conditions for the growing-in of the prosthesis, thereby increasing the stress resistance of an implant.

FIG. 4a shows, in the side view of a proximal portion of the prosthesis as illustrated in FIG. 4, a circular opening 8' in the shank side wall 3. The openings in the side walls of the shank may be suitably used for mounting cylindrical support members (cf. positions 2, 3, 8.1 shown in FIG. 4) by means of which the implanted prosthesis may be supported on either side, on the inner bone wall. Support members made of endogenic spongiosa or bioporous foreign material, for example hydroxyapatite ceramic material, both ensure a safe growing-in of the endoprosthesis and enable a particularly high mechanical stress resistance of the implant.

The invention is not limited to the above preferred embodiment. Rather, there are a number of possible variants which make use of the above solution even, in completely different constructions.

What is claimed is:

1. An endoprosthesis for a cement free anchorage in a bone having a longitudinal direction, comprising:
   a prosthetic shank to be secured in the bone in the longitudinal direction of the bone and having a proximal end and a distal end, the prosthetic shank comprising three plate-like blades arranged in parallel and presenting a cross-sectional profile that has an open configuration, a first one of the blades constituting a central web and a second and third ones of the blades constituting side walls which enclose, at least partially, the central web and extend, at least partially, in parallel, in a direction of the central web, the prosthetic shank further including bridges connecting the side walls with the central web, wherein a region adjacent the distal end of the prosthetic shank is in the shape of a scoop and the blades are joined at least at the distal end to form a common cutting edge; and a collar including a pin for receiving a ball joint attached to the proximal end of the prosthetic shank.

2. The endoprosthesis according to claim 1, wherein the central web has a central plane that is parallel with the side walls and the pin is arranged on the collar to have a central axis that lies in an extension of the central plane of the central web.

3. The endoprosthesis according to claim 1, wherein the blades are tapered in a streamlined fashion toward the distal end and having a rounded configuration.

4. The endoprosthesis according to claim 3, wherein the blades each have a medial edge that is substantially S-shaped when viewed from a side of the prosthetic shank.

5. The endoprosthesis according to claim 1, wherein the cross-sectional profile is substantially m-shaped.

6. The endoprosthesis according to claim 5, wherein the central web projects medially beyond the side walls.

7. The endoprosthesis according to claim 1, wherein the bridges are web-like and have distally oriented cutting edges.

8. The endoprosthesis according to claim 1, wherein each side wall delimits a space between itself and the central web and the prosthetic shank has openings at the proximal end that communicate with a respective one of the spaces between the side walls and the central web.

9. The endoprosthesis according to claim 8, wherein one of the openings is associated with each one of the spaces.

10. The endoprosthesis according to claim 8, wherein the openings are in the form of elongated holes that extend from a medial to a lateral direction of the prosthetic shank.

11. The endoprosthesis according to claim 10, wherein the holes are parallel to one another and are surrounded by rounded-off edges.

12. The endoprosthesis according to claim 1, wherein each of the side walls has an opening and a recess in a region near the proximal end of the prosthetic shank.

13. The endoprosthesis according to claim 12, wherein the recess in each side wall has a form of a circular segment which opens laterally and the opening in each side wall has one of a triangular and circular shape.

14. The endoprosthesis according to claim 13, further including support members mounted in the openings and extending at right angles to the longitudinal direction of the prosthetic shank.

15. The endoprosthesis according to claim 14, wherein the support members comprise one of spongiosa and bioporous material.

16. The endoprosthesis according to claim 1, wherein the prosthetic shank has a proximal region that includes a lateral wall that is only partially closed.

17. The endoprosthesis according to claim 16, wherein the lateral wall has elongated slots that extend parallel to the longitudinal direction of the prosthetic shank.

18. The endoprosthesis according to claim 1, wherein the endoprosthesis comprises a titanium material and is a vacuum cast product.

19. The endoprosthesis according to claim 1, wherein the blades of the prosthetic shank have rough surfaces.

20. The endoprosthesis according to claim 19, wherein the rough surfaces are as a result of sand blasting.

21. The endoprosthesis according to claim 19, wherein the blades each include a coating of bioporous material which constitutes the rough surfaces.

22. The endoprosthesis according to claim 21, wherein the coating comprises one of a hydroxyapatite ceramic and a plasma spray with a layer thickness of 50 to 100 micrometers.

* * * * *